United States Patent [19]

Shields

[11] Patent Number: 5,176,657
[45] Date of Patent: Jan. 5, 1993

[54] SHOT GUN SYRINGE WITH CARTRIDGE AND SCABBARDS

[76] Inventor: Jack W. Shields, 1950 Las Tunas Rd., Santa Barbara, Calif. 93103

[21] Appl. No.: 821,178

[22] Filed: Jan. 15, 1992

[51] Int. Cl.⁵ .............................................. A61M 5/00
[52] U.S. Cl. ................................ 604/232; 604/192; 604/197; 604/263
[58] Field of Search .............................. 128/917, 919; 604/232-235, 263, 187, 197-199, 192, 194

[56] References Cited

U.S. PATENT DOCUMENTS

| | | | |
|---|---|---|---|
| 2,672,142 | 3/1954 | Melton | 604/233 |
| 3,008,570 | 11/1961 | Roehr et al. | 604/197 |
| 4,592,744 | 6/1986 | Jagger et al. | 604/192 |
| 4,892,525 | 1/1990 | Hermann, Jr. et al. | 604/263 |
| 4,915,701 | 4/1990 | Halkyard | 604/232 |
| 5,061,179 | 10/1991 | Dragan . | |

*Primary Examiner*—C. Fred Rosenbaum
*Assistant Examiner*—Ronald K. Stright, Jr.

[57] ABSTRACT

Syringes using pre-loaded cartridges for injecting fluid medications can be made safer for users and patients, more compliant with modern infection-control precautions, and easier to operate by supplying thumb-ring activated, breech-loading syrettes with screw-on plungers for aspirating into and emptying transparent cartridges with permanently attached needles. The cartridges can be made with trailing terminal circular flanges with gaps for stabilizing the cartridge in the syrette breech chambers closed by hinging breech blocks; permanently attached leading needles whose exposed tips are kept sterile before use by thin disposable elastomeric scabbards; and whose trailing ends optimize visualization of flashback. Such "shot-guns" consisting of reusable breech-loading syrettes and disposable pre-loaded transparent cartridges with attached needles can be supplied with two part puncture resistant plastic scabbard systems and trailing caps which integrate to keep the cartridges and needles sterile before use; which can be used as a convenient sterile holders for loaded or partially unloaded cartridges inside the syrettes, and which implement safe ejection of empty disposable cartridges with permanently attached needles from the breech chambers of the syrettes into sharps containers, thereby minimizing opportunities for hazardous needle-stick injuries.

4 Claims, 3 Drawing Sheets

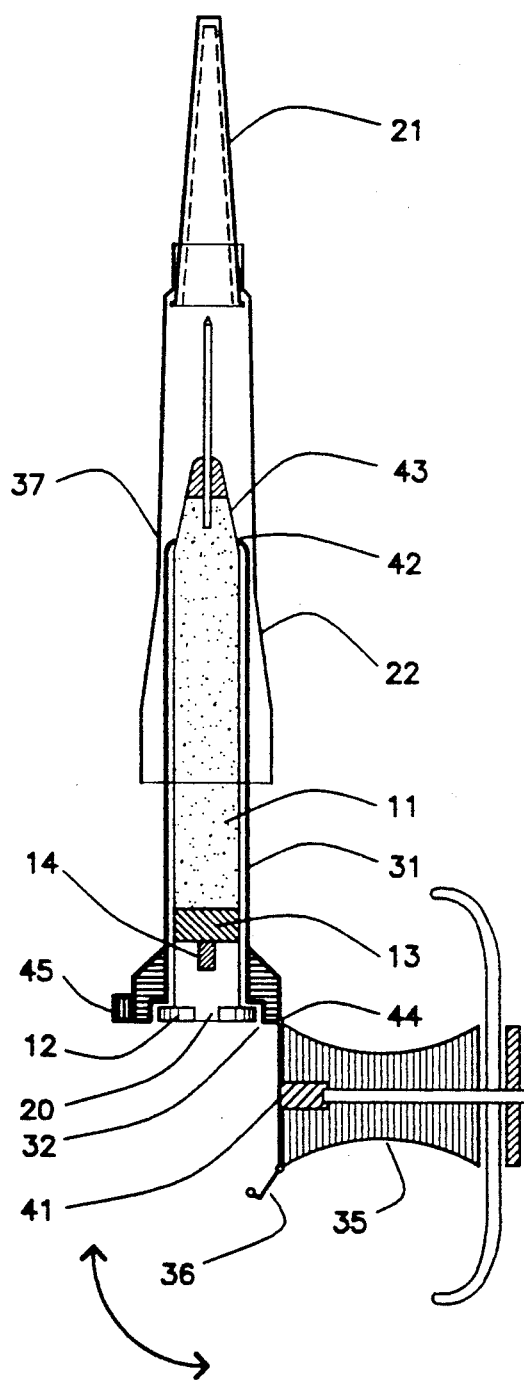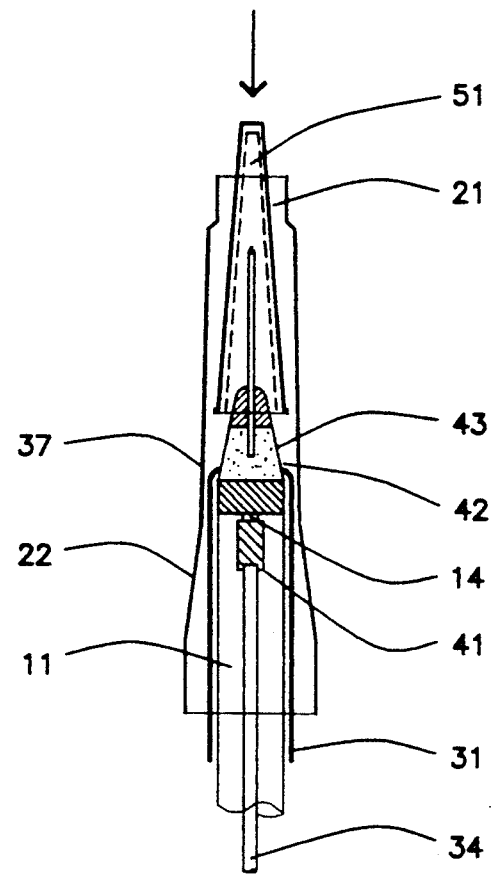
Fig. 5
Fig. 4

SHOT GUN SYRINGE WITH CARTRIDGE AND SCABBARDS

BACKGROUND OF INVENTION

1. Field of Invention

This invention relates to the prevention of accidental needle-stick injuries wherein health care workers (HCW) become infected with blood-borne pathogens, such as human immuno-deficiency viruses (HIV), hepatitis B viruses (HBV, hepatitis C viruses (HCV), herpes simplex viruses (HSV), Epstein-Barr viruses (EBV), etc.; and wherein patients become infected by such pathogens carried in the blood of an infected HCW, or a HCW accidentlly needle stuck during use of a syringe for injecting the contents of a fluid-filled cartridge.

2. Description of the Prior Art

The use of cartridge-loaded syrettes to inject the contents of cartridges containing fluid medications, especially penicillin, morphine or cocaine derivatives, through cartridges with permanently attached needles has been common medical practice since World War II. There are two kinds of such cartridge-loaded syrettes in common use: side-loading and breech-loading. A breech-loading syrette customarily has a cartridge receiving chamber in the trailing end of its barrel for in-loading cartridges with permanently attached needles, and a hinged metal breech-block containing a sliding plunger for expelling fluid from the cartridge. The barrel has a large-bore aperture on the leading end which securely holds the expanded hub of a leading needle by means of matching threads. (See U.S. Pat. No. 2,778,359 issued Jan. 22, 1957 to Friedman). The most commonly used models are metallic "Tubex" brand syrettes made by Wyeth. Plastic side-loading models, such as Wyeth Tubex Fast-Trak Syringe, quick-loading; and Wyeth-Ayerst Tubex Injector (U.S. Pat. No. 4,642,103 issued Jan. 7, 1986 to Gettig) are now available. However, the former is not suited to easy and safe disposal of the cartridge with an attached needle; while the latter projects an unprotected glass or plastic cartridge/needle into chosen sites customarily outside of the mouth. Because the cartridge is usually made of glass, and the leading end attached to the needle is fragile, such unitized cartridges are not suited for dental use.

The fundamental features of such reusable medical syrettes are to allow single injections of pre-measured quantities of fluid or semi-fluid medications with minimal opportunity for contamination of such fluids or the injecting needle before or during the course of injection into a patient. However, there are hazards inherent for the user, owing to possible needle-stick injury prior to safe disposal of the spent unitized cartridge/needle. These hazards are addressed through provision of attachable two part scabbards for standard metallic and plastic syrettes and syringes. Since 1950 a modified syrette, commonly known as the "Carpule Aspirator" has become the standard means for giving dental anesthesia in the U.S. and in other nations. The "Carpule Aspirator" has advantages over the "Tubex" syringe in that the trailing end of the syringe plunger is supplied with a thumb-ring which allows the user to aspirate or inject with one hand, while feeling for anatomical landmarks with the other. For the dental user, the "Carpule Aspirator" has other advantages in that the plunger inside the carpule is activated by an arrow-head which pierces and holds the plunger and, thus, is quicker to attach than a threaded mechanism on the trailing end of the inside plunger. Because injections for insuring adequate dental anesthesia are often into several different sites, and often require one or more reloading of carpules, this would seem advantageous. However, the "Carpule Aspirator" syringe has disadvantages, because the carpules which load through the side are not supplied with permanently attached needles. Therefore, the leading end of the "Carpule Aspirator" barrel is threaded to receive a double-ended needle which is manually screwed on and detached at the leading end of the syrette. The assembly is easy and inexpensive to use, but provides needle-stick hazards for the dental client, as well as the dentist and co-workers which are outlined in the MMWR: Recommended Infection-Control Practices for Dentistry Apr. 18, 1986 Vol. 35/#15:237-242 whose relevant portions read as follows:

1. Sharp items (needles, scalpel blades, and other sharp instruments) should be considered as potentially infective and must be handled with extrordinary care to prevent unintentional injuries.

2. Disposable syringes and needles, scalpel blades, and other sharp items must be placed into puncture-resistant containers located as close as practical to the area in which they were used. To prevent needlestick injuries, disposable needles should not be recapped; purposefully bent or broken; removed from disposable syringes; or otherwise manipulated by hand after use.

3. Recapping of a needle increases the risk of unintentional needlestick injury. There is no evidence to suggest that reusable aspirating-type syringes used in dentistry should be handled differently from other syringes. Needles of these devices should not be recapped, bent, or broken before disposal.

4. Because certain dental procedures on an individual patient may require multiple injections of anesthetic or other medications from a single syringe, it would be more prudent to place the unsheathed needle into a "sterile field" between injections rather than to recap the needle between injections. A new (sterile) syringe and a fresh solution should be used for each patient.

In order to arm such a "Carpule Aspirator" syringe with the double-ended needle used for draining carpules and injecting anesthetic, the user must use two hands to screw on said double-ended needle to cap the leading end of said syringe. Between injections with the same needle to empty one or more carpules, the leading tip of said double-ended needle must not be recapped using two hands, and is better left in a sterile field which might not be easy to maintain. After final use, the leading tip of said double-ended needle must be recapped using two hands in order to uncap the leading end of said syringe before said double-ended needle can be disposed safely into a sharps container. In short: dentists should not needle-cup syrettes or re-cap double ended needles.

Recognizing the hazards of attaching double-end needles to dental syrettes, in U.S. Pat. No. 4,334,536 issued Jun. 15, 1982, Pfeger described pre-filled syringes in which the means for attaching the needle assembly to the syringe, the needle cover and the activating mechanism are unitized, but breakable at specific points to expose the needle and empty the syringe. However, Pfeger provided no means for safely protecting the needle after use. In U.S. Pat. No. 4,767,413 issued Aug. 30, 1988. Haber et al described a disposable dental syrette which manually retracts and safely re-sheaths the needle back into the syrette after the cartridge contents have been injected. Such syrettes are considered to be user-safe with respect to needle stick injuries, but can not be re-used and, hence, expensive. In U.S. Pat. No. 5,007,901 issued Apr. 16, 1991 a method is described for safely retracting a detachable needle used for insertion of an intravenous catheter into a disposable syringe to protect the patient and the user during and after use, but this assembly is not suitable for dentists, especially for giving single injections into multiple sites.

The barrels and muzzles of reusable medical and dental syringes or syrettes are not customarily supplied with any kind of scabbard; and are normally autoclaved before reuse. However, disposable medical luer-lock syringes with detachable needles, such as "Monoject" brand produced by Sherwood Medical Corporation are customarily encased in capped puncture-resistant plastic scabbards which keep the syringes and pre-attached needles sterile before use; and which can be reused to recap the needle, as well as the entire syringe after use. Such scabbards can be used to safely dispose of the used needles and syringes into sharps containers, but the fitting of parts, relative diameters and mode of operation differ from those described here. In brief, the "Monoject" system uses the hub of the injection needle as the focal point for the interplay of frictional forces during a two-handed recapping of the needle; whereas the co-pending invention uses the leading tip of a syringe as a large focal point to hold the leading portion of the armed syringe by impaction in a puncture resistant scabbard until ejected by manual control or gravity into a convenient sharps container.

In addition, Sherwood Medical produces a disposable "418" dental injector with a reusable plastic holder, similar to the Wyeth Tubex Injector (U.S. Pat. No. 4,642,103), to securely hold the trailing end of the injector which, in turn, is made to empty a 1.8 ml. standard carpule by means of a plunger with a customary arrowhead configuration and a double-ended needle permanently attached to the leading end of the injector. After the carpule is emptied via the double-ended needle, the injector is replaced into the puncture-resistant scabbard wherein it was originally packaged; the reusable plastic holder is manually detached; and, then, the disposable holder and carpule are disposed into a sharps container. With respect to needle-stick injuries, this "418" assembly is theoretically much safer than the standard metal "Carpule Aspirator" syringes to which double-ended needles must be bi-manually attached and detached by means of threads. However, the "418" is difficult to manipulate during attachment and detachment of the plastic holder; during reinsertion of the needle and trailing injector into the original scabbard; and during manipulation of the plunger, especially when the arrowhead becomes mis-aligned.

During the last three years, major manufacturers of luer-lock syringes have manufactured sliding plastic scabbards permanently attached to standard disposable luer-lock syringes. After use of the syringe/needle in a patient, the plastic scabbard is advanced over the barrel of the syringe, usually using two hands, such that the leading open end of the scabbard extends beyond the tip of the needle and, then, maintained there by a locking mechanism between the barrel of the syringe and the scabbard which slides over. The disadvantages of such assemblies are that they are not easy to use with one hand, the locking mechanism between syringe and over-riding scabbard is complex, the cost is 1.5 to 2 times as much as that of the original disposable luer-lock syringe lacking a permanently-attached sliding scabbard, and are not easily adapted to dental use or reuse for giving more than one injection.

The addition of a circular external flange to the trailing end of a pre-loaded unitized cartridge/needle intended for injecting dental anesthetics or solutions under sterile conditions by means of a reusable syringe with an activating plunger is novel, at least in the current practice of administering dental anesthesia. Alexandre in U.S. Pat. No. 4,944,677 (JUL. 31, 1990) describes a flange which connects a dental mandrel to the motor and a mandrel for fabricating of such apparatus from a conventional disposable dental needle. Dragan in U.S. Pat. No. 5,061,179 (Oct. 29, 1991) describes a flange which locks the trailing end of a cartridge to the trailing chamber in a manually operated dental extruder for viscous material so that the cartridge can not become detached or become wedged between flexible side walls.

A gap in the circular flange for fitting a projection in the chamber of a dental syringe, such that the cartridge can not rotate and the bevel of the needle is maintained in a constant position with respect to a dental syrette, is also novel. However, in the Monoject "418" dental injector, two flanges are placed near the trailing end of the injector to provide attachments for a reusable plastic holder. Such flanges are placed near, but not at the trailing end of the injector; and do not resemble the circular flanges which form the trailing end or "rim" of a rifle or shot gun cartridge.

Similarly, a corresponding modification of the trailing end of the chamber of a breech-loading reusable dental syrette to receive the circular flange and hold the slot in fixed position, appears novel. Therefore, it is cogent to described mechanical modifications in syrettes which will help users to employ such integrated modifications efficiently at minimal cost to patients.

SUMMARY

The object of this invention is to provide health care workers, especially dentists, with combinations of reusable syrettes, preloaded cartridges with permanently attached needles and disposable puncture resistant scabbards which will maximize sterility and minimize the chances of needle-stick injuries during use in the care of patients.

Another object is to provide an improved system for preventing the transmission of blood-borne infectious diseases from health care workers to patients during the performance of invasive procedures requiring the administration of local anesthesia.

A third object is to provide dentists and surgeions with an improved local anesthesia system which is easy to use, efficient, inexpensive and is comfortable for users and clients.

A fourth object is to provide dentists and their assistants with an integrated system for giving local anesthesia compliant with MMWR-recommended infection-control practices, quoted verbatim on page 4, lines 3-19.

BRIEF DESCRIPTION OF THE DRAWINGS

FIG. 4 is an axial section of a loaded cartridge when ready for use in the barrel of a breech-loading dental syrette with a hinging breech-block and latch.

FIG. 5 is an emptied cartridge just prior to ejection, but before the plunger system is dissembled.

DESCRIPTION OF THE PREFERRED EMBODIMENTS

Figure 1:
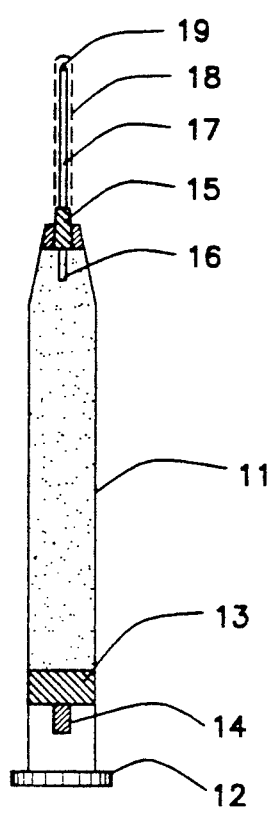
FIG. 1 is an axial section of a full cartridge with attached needle.

A first preferred embodiment of the "shot gun" cartridge is shown in FIG. 1. A prefilled cartridge (11) with a trailing terminal flange (12) is activated by an inside piston (13) with a trailing screw-on male fitting (14) which mates with a female counterpart on the leading end of a thumb-activated syrette plunger. Aspiration before injection, and the injection of fluid from the cartridge is performed by means of a permanently attached needle (15) whose trailing end (16) provides optimal visualization of blood "flash-back" during aspiration; and whose leading end (17) is sheathed by a disposable small caliber, closed-ended elastomeric tube (18) which extends just beyond the sharp tip of the beveled needle (19) in order to maintain optimal sterility until the needle is inserted into the intended site in a patient. As shown below, the flange (12) on the trailing terminal end of the cartridge (11) is made with a gap (20) which mates with a corresponding projection in the chamber of the syrette, such that the cartridge can not rotate and such that the bevel of the exposed needle (19) is maintained in a constant position with respect to the syrette as a whole.

Figure 2:
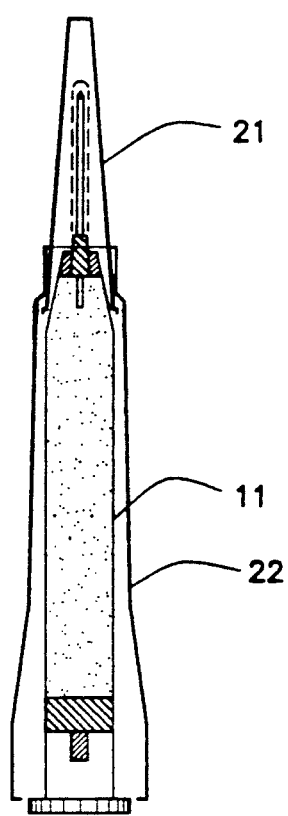
FIG. 2 is an axial section of a full cartridge encased in a puncture-resistant two part conical scabbard.
Figure 1A:
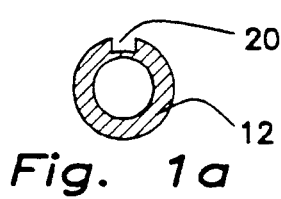
FIG. 1a is a cross section through a circular flange at the trailing end. (Scale 1:1).
Figure 2A:
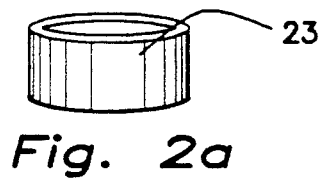
FIG. 2a is a cap for the trailing scabbard.

As shown in FIG. 2, the loaded cartridge with attached needle is supplied within a two part puncture-resistant tubular scabbard system consisting of a leading conical scabbard (21) whose trailing aperture is smaller than the base of the conical leading end of the needle hub; and a larger graded conical scabbard (22) whose leading open end attaches by friction to the trailing end of the leading scabbard, but is smaller in leading internal diameter than the external diameter of the trailing end of said leading conical scabbard. A removable cap (23) attaches by friction to the trailing end of the larger scabbard (22) in order to augment sterility and enclose the cartridge (11) before use. The interior empty cone of leading scabbard (21) is large enough to house the leading end of the needle and its elastomeric tubular cover and extends significantly beyond the leading tip of said needle and said elastomeric tube.

Figure 3:
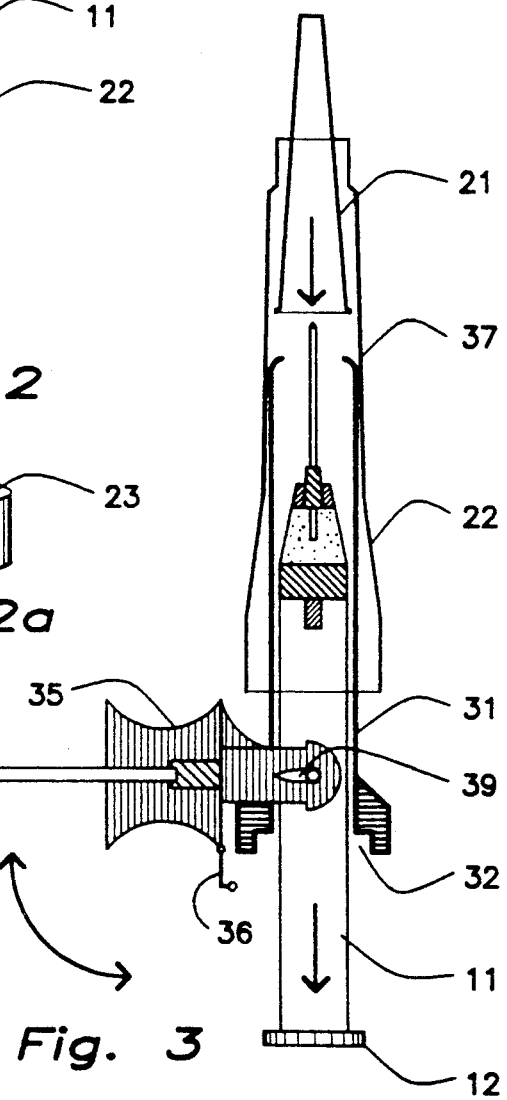
FIG. 3 is an axial section of a partly ejected spent cartridge after the leading end of a breech-loaded syrette has been inserted into the two part scabbard system and the leading scabbard has been pushed toward the breech.
Figure 3A:
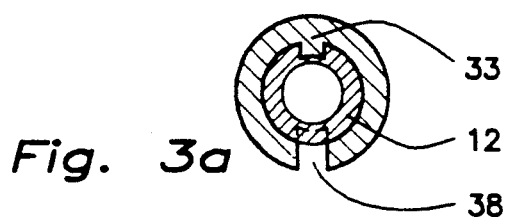
FIG. 3a is a cross section of the trailing portion of the breech chamber.

As shown in FIG. 3, the "shot-gun" cartridge with attached needle (11) is unloaded from and loaded into a breech-loading syrette (31) whose breech chamber portion (32) holds the terminal circular flange (12) on the cartridge; and contains a projection (33) which fits the gap (20) [Compare FIG. 1 and FIG. 3 (below)] in the flange to prevent rotation of the cartridge and attached needle after the rigid plunger (34) and breech-block (35) portions are swung in the direction of arrow into alignment with the long axis of the syrette (31). Locking in the use position wherein the cartridge cannot rotate, move forward or move backward is enabled by a hinged latch (36) on the rim of the breech block (35).

Also, as shown in FIG. 3, safe unloading of a spent cartridge (11) after use is accomplished by inserting the exposed needle and leading end of the syrette (31) into the trailing conical cartridge scabbard (22) until the leading end of the syrette binds by friction at a critical point (37). It will be found that the frictional bond between the leading end of a metal syrette and the internal cone of the plastic scabbard is tight, such that the assembly can be left safely until unloading is convenient. When the time is proper to unload, displacement of the leading conical scabbard (21) in the direction of the arrow, will secondarily displace the needle, needle hub and cartridge backward through the trailing barrel and the breech of the syrette (31). This happens when the trailing open end of the leading conical scabbard contacts and pushes, but does not slide onto the wider base of the needle hub. The cartridge with attached needle will be pushed backward only a short distance, but a distance sufficient to disengage the trailing terminal flange of the cartridge from the breech chamber (32). As a result, the cartridge/needle will fall safely without impedance under the influence of gravity into an appropriate sharps container. In case of a jammed needle, a fail-safe mechanism is provided by making an indentation (38) in the breech chamber portion on the opposite side from the projection (33). The indentation (38) should be large enough to accommodate the tip of forceps suitable for extracting the cartridge from the breech chamber by grasping the trailing flange (12).

As shown in FIG. 4, when the syrette (31) is properly loaded with a full cartridge (11) whose terminal flange (12) is seated in the receptacle of the syrette chamber portion (32), a female screw-on component (41) on the leading end of the syrette plunger (34) engages the male screw-on component (14) in the trailing of the plunger inside the cartridge to provide for smooth action and control during aspiration into, as well as emptying of the cartridge. Appropriate internal sizing of the aperture (42) at the leading end of the syrette in relation to coning of the leading end of the cartridge, will make combined actions smooth and simple. It should be emphasized that the choices of rigid metal and plastic components is critical, especially when the leading conical scabbard (21) must not slide on far enough to actually grasp the conical hub (43) holding exposed parts of the needle, or slide through the aperture (42) which engages the cartridge within and attached needle beyond the barrel of the syrette, as shown in more detail in FIG. 5, after the leading cone has been displaced from contact with the trailing cone in the direction of the arrow. A significant space beyond the tip of the needle (51) in the leading conical scabbard (21) assures that the trailing end of the scabbard will push on the exposed portion of the needle hub before the leading end touches the tip of the needle and, also, provides sufficient thrust in the direction of the arrow. These relationships are shown in extended, exaggerated fashion in FIG. 3.

Also, as shown in FIG. 4, the breech-block portion of a breech-loading syrette can be hinged on one side (44), closed securely, and latched by means of a hinging latch (36) which inserts into an appropriate latch housing on the other (45). Alternatively, if the breech block portion is hinged from a post located forward along the barrel, as shown in FIG. 3, the hinging mechanism requires a slot (39) through which the arms of a swinging block can be extended to clear the rim of the breech chamber, before the swinging block is securely latched down.

Figure 6:
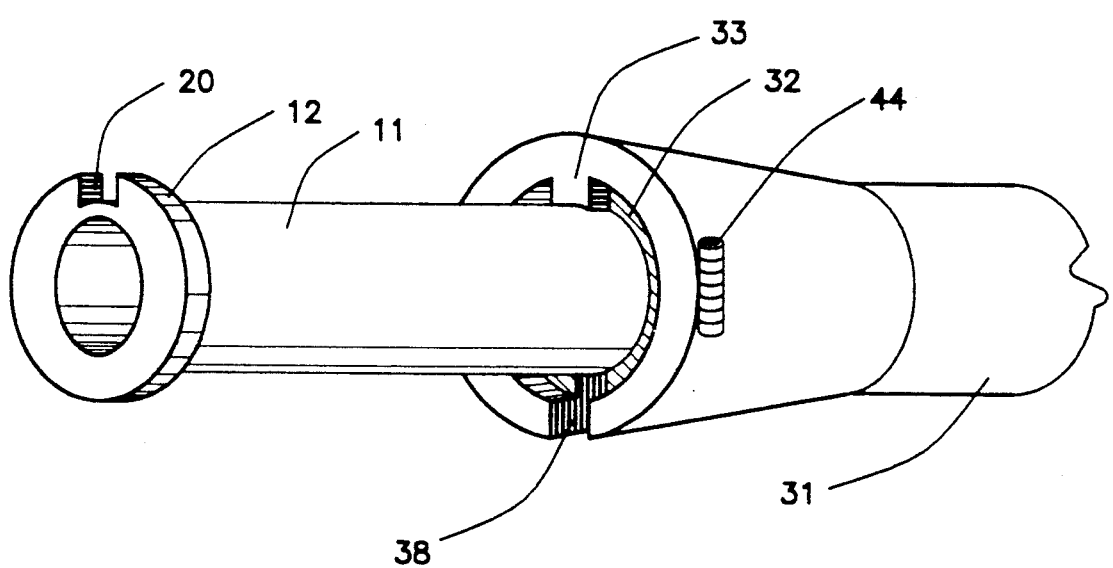
FIG. 6 is an oblique detail of the cartridge partly inserted into the breech chamber portion of this breech-loading syrette. (Scale 2:1).

As shown in detail in FIG. 6, when the cartridge (11) is inserted into the expanded breech chamber component (32) of the syrette, the gap (20) in the trailing terminal flange (12) will be engaged by the projection (33) in the breech chamber (32) with a hinge (44). On the opposite side of the chamber, 180° away, an indentaion in the chamber (38) provides mechanical access to the circular flange in the case of jamming during ejection.

In detailed operation, a full "shot gun" cartridge with attached needle (11) is removed from its two part scabbard system (21-23) by manually removing the trailing disposable cap (23) and grasping the trailing flange (12) to insert the leading needle (17) and elastomeric scabbard (18) into the breech of the syrette (31). When the trailing flange (12) is properly seated in the breech chamber (32) and rotated until the slot or gap (20) engages the projection (33) in the trailing chamber, the breech is locked by swinging the plunger (34) into the long axis of the cartridge (11) and closing the latch (36) into its housing (45). The syrette plunger is then advanced in this long axis until its leading screw-on mechanism (41) engages the mating part (14) on the inside cartridge plunger (13); and is screwed on by right-hand threads until fully engaged. Held securely by the trailing flange (12) and fitting breech components, as well as by appropriate sizing of the aperture (42) in the leading end of the syrette (31), the assembly is ready for use or reuse in a selected site, after the elastomeric sheath (18) is disposed from the leading end of the needle (17) whose bevel (19) is maintained in a constant known position by all the aforementioned components (12,20,31,32,33,42).

After customary use, or between uses in a selected anesthetic field, the syrette with a projecting unprotected needle can be replaced into the leading portions (21,22) of the conical puncture-resistant scabbard system whose trailing aperture presents a big diameter (e.g. ±2 cm.), and whose leading portions are made to provide smooth insertion without hang-ups, as well as a secure bond between the larger conical scabbard (22) and the leading end of the syrette at a critical point (37). Proper selection of semi-rigid and rigid integral components, as well as cone sizing, are essential.

When the cartridge contents are spent or sufficient fluid contents have been expended, the used cartridge with attached needle can be disposed safely into a conveniently located sharps container by unscrewing the leading tip of the rigid plunger (41) from its mating fitting (14) in the semi-rigid piston (13) activating the cartridge; unlocking the breech-block of the syrette (36,45); pulling back and swinging the plunger (34) 90° away from the barrel of the syrette; and pushing the leading scabbard (21) to eject the cartridge backward through the breech portion before the friction bond at point (37) between the leading tip of the syrette (31) and the larger trailing conical scabbard (22) is loosened. After the spent cartridge and attached needle are safely ejected, the leading scabbards (21,22) can be safely discarded. The reusable syrette (31) can be properly cleansed or autoclaved and used over and over again, especially if made from durable material.

An outstanding feature of this "shot-gun" assembly is that the same breech-loading syrette (31) can be loaded, safely stored and unloaded repeatedly, safely and quickly for use in different sites in a given patient. Use is like "breaking the breech" to load and reload a standard 410 gauge single-barreled shot gun. However, as opposed to a spent cartridge originally filled with a detonating cap, powder and shot, it would be hazardous to have an automatic ejector for an empty fluid-filled cartridge still armed with a potentially contaminated needle. Therefore, one is obliged to unload from the leading end of the breech-loading syrette by means of the leading conical scabbard which serves more or less like a ram-rod, as shown. In the unusual case of a bent needle capable of jamming the ejection mechanism, the breech chamber portion is provided with an indentation (38), 180° opposite from the projection (33), to provide mechanical access whereby the cartridge can be extracted safely by grasping the terminal circular flange with forceps.

In summary, then, medical and dental syringes which in-load cartridges for injecting anesthetics or other fluid medications can be made safer, easier to use and more compliant with MMWR-recommended infection-control precautions by the following modifications:

1. Using a pre-loaded cartridge wherein the injection needle at the leading end is permanently attached to the leading end of the cartridge.

2. Making the trailing end of the injection needle clearly visible inside the cartridge, such that the "flashback" of aspirated blood can be seen immediately, if the needle entered a vessel.

3. Supplying the cartridge with an inside plunger whose excursions are manipulated by a matingly threaded plunger comprising a central component of a hinging breech-block in a thumb-ring activated breech-loading dental syrette.

4. Supplying the cartridge with a trailing terminal circular flange which precisely fits the expanded chamber portion in said hinged, breech-loading syrette wherein a hinged breech-block latches over securely to prevent backward or forward motion of the cartridge.

5. Making a gap in the circular flange at the trailing terminal of the cartridge which fits a projection in the chamber portion of the syrette breech, such that the cartridge can not rotate, and such that the bevel of the leading needle is maintained in a constant predictable position.

6. Making an indentation in the opposite side of the breech chamber, so that a spent cartridge can be extracted with forceps, in case a bent needle or other equipment failure jams the ejection mechanism.

7. Supplying the leading end of the injection needle with a small-bore, closed-ended, disposable elastomeric tube to keep the needle sterile until insertion into an intended site.

8. Supplying the cartridge and attached needle with a puncture-resistant two part conical scabbard which progressively serves as a sterile container for the pre-loaded cartridge and needle; as a sterile receptacle for holding the loaded syringe in a sterile field between injections; and as a guard for the leading tip of the needle and leading end of syringe until the spent cartridge with attached needle is ejected safely from the breech of the syrette into a suitable sharps container by backward force on the leading end of these integrated conical scabbards.

Although this "shot gun" fluid injection assembly has been described partly in terms of specific embodiments with relative diameters and lengths, such embodiments are exemplary only, and not intended to be limiting. It will be appreciated by those skilled in the art that wide variations in details and materials can be made without departing from the spirit of the invention.

I claim:

1. An assembly for injecting measured fluid medications comprising, in combination:
   (a) a transparent medicament containing cartridge, said cartridge comprising a cylindrical body portion having a leading end forming a conical hub; a beveled-tip needle permanently attached in said conical hub; a trailing end terminating in a circular flange, said circular flange having a greater outer diameter than the outer diameter of the body portion, said circular flange having a single longitudinal gap therein; and an inside piston having a trailing threaded member projecting therefrom; and
   (b) a breech-loading syringe comprising a thumb-activated plunger, said plunger having a leading end with a threaded member mating with said trailing threaded member on said inside piston and a trailing end terminating in a thumb-ring; the breech-loading syringe also comprising a leading end whose circular aperture precisely fits the base of said conical hub of said cartridge, a trailing hollow cylindrical barrel dimensioned to accommodate said body portion of said cartridge within the barrel, said barrel having an expanded trailing chamber portion, said expanded trailing chamber portion having a projection on the trailing surface thereof and an indentation substantially 180° from said projection, said indentation providing mechanical access to the said trailing terminal circular flange of said cartridge, said projection being dimensioned to matingly engage said single longitudinal gap in said trailing terminal circular flange of said cartridge when the leading end and body of said cartridge is fully inserted into said barrel; said cartridge being secured within said syringe by a hinged breech block portion containing an axial passage therethrough holding said thumb-activated plunger and a latch which latches to cover said expanded trailing chamber.

2. The assembly of claim 1 further comprising a two part disposable puncture-resistant scabbard assembly comprising two hollow cones of increasing diameter wherein:
   (a) a first cone has a closed leading end trailed by a conical cavity larger and significantly longer than the exposed portion of said beveled-tip needle, a trailing internal diameter smaller than that of the mid-portion of said conical needle hub, and a trailing external diameter larger than that of said circular aperture in the leading end of said syringe; and
   (b) a second cone has an open leading end which releasably engages the trailing end of said first cone, a leading circular aperture with a diameter smaller than that of the trailing external diameter of said first cone, a middle portion which encloses said cartridge prior to use, the cavity of said middle portion becoming smaller in diameter than the diameter of the leading end of said syringe point, and a cylindrical trailing end of relatively large diameter;

and a trailing cap matingly and releasably engagable said cylindrical trailing end of said second cone, thereby sealing the trailing end of said disposable puncture-resistant scabbard assembly.

3. The assembly of claim 1 further comprising a small bore elastomeric tube which is releasably attached to the leading portion of said conical hub of said needle and is closed just beyond the beveled tip of said needle for safely protecting said needle prior to use.

4. The assembly of claim 1 wherein the trailing end of said permanently attached needle projects visibly into the leading end of said transparent cartridge, but not far enough to interfere with the excursion of said inside piston.

* * * * *